United States Patent [19]

Krumme

[11] Patent Number: 5,164,972
[45] Date of Patent: Nov. 17, 1992

[54] COMPUTER TOMOGRAPHY APPARATUS HAVING AN ANNULARLY GUIDED ELECTRON BEAM

[75] Inventor: Hans-Jochen Krumme, Uttenreuth, Fed. Rep. of Germany

[73] Assignee: Siemens Aktiengesellschaft, Munich, Fed. Rep. of Germany

[21] Appl. No.: 769,800

[22] Filed: Oct. 2, 1991

[30] Foreign Application Priority Data

Oct. 15, 1990 [EP] European Pat. Off. ........ 90119743.4

[51] Int. Cl.⁵ .............................................. H05G 1/60
[52] U.S. Cl. ...................................... 370/10; 378/137
[58] Field of Search ................................. 378/10, 137

[56] References Cited

U.S. PATENT DOCUMENTS 3,919,550  11/1975  Banbury.
4,158,142  6/1979  Haimson.

FOREIGN PATENT DOCUMENTS 0232056  8/1987  European Pat. Off. .
61-68032  8/1986  Japan ..................... 378/10
2044985  10/1980  United Kingdom .

Primary Examiner—Craig E. Church
Attorney, Agent, or Firm—Hill, Van Santen, Steadman & Simpson

[57] ABSTRACT

In a computer tomography apparatus having an annularly guided electron beam, has an x-ray source with an annular anode. Before the beginning of a scan event, the electron beam travels through the x-ray source concentrically relative to the annular anode until it is incident on a beam catcher at the closed end of the x-ray source. Proceeding from the end of the x-ray source at which the beam catcher is disposed, the electron beam is focused on, and scans, the annular anode. A constant focus size of the electron beam on the annular anode is thereby achieved.

5 Claims, 1 Drawing Sheet

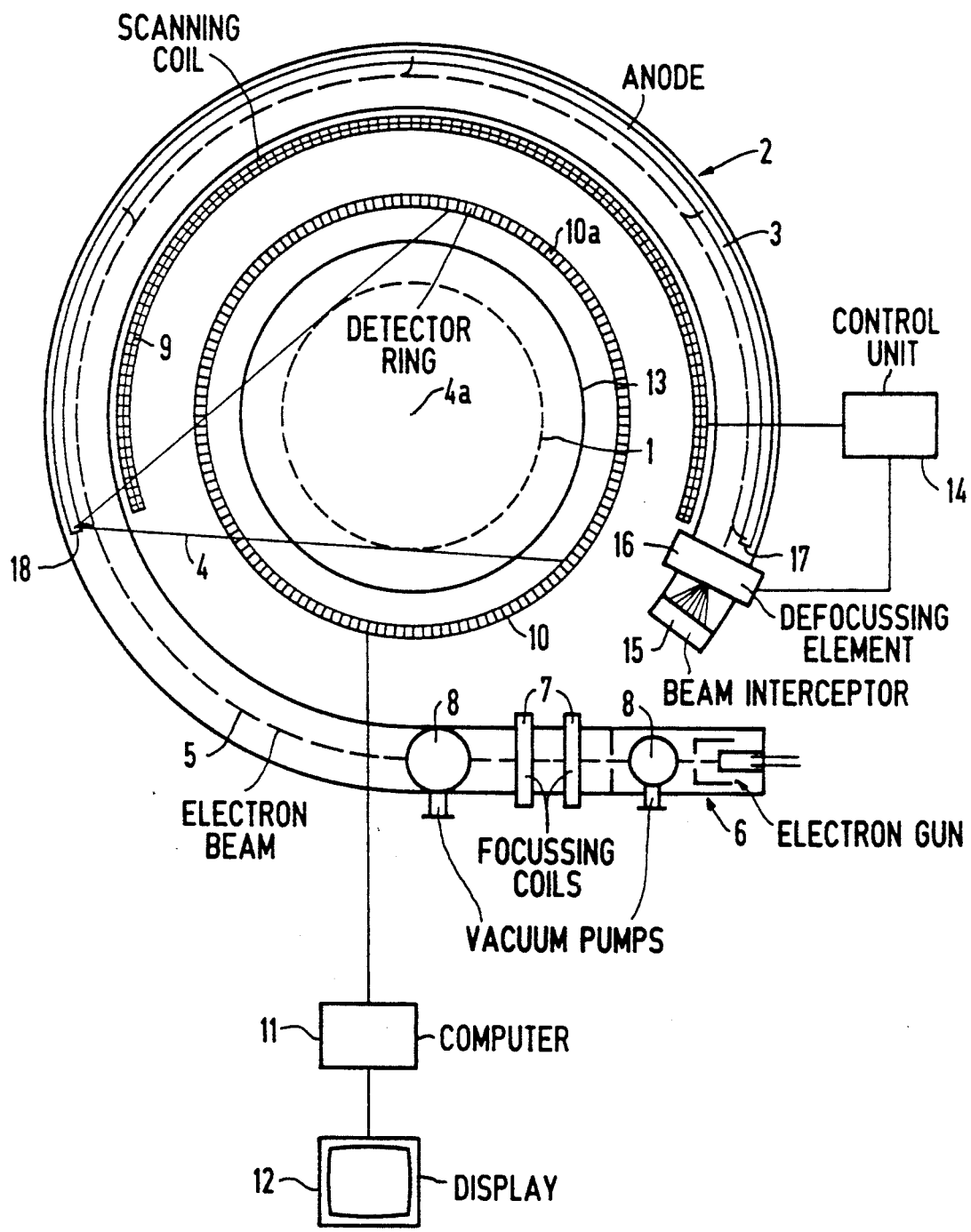

COMPUTER TOMOGRAPHY APPARATUS HAVING AN ANNULARLY GUIDED ELECTRON BEAM

BACKGROUND OF THE INVENTION

1. Field of the Invention

The present invention is directed to a computer tomography apparatus, and in particular to a computer tomography apparatus having an annularly guided electron beam.

2. Description of the Prior Art

Computer tomography systems are known having an annular x-ray source surrounding a measuring field. The x-ray source has an annular electrode, which is scanned by an electron beam for generating a rotating x-ray beam. The electron gun for injecting the electron beam is disposed on the central axis of the measuring field, which is coincident with the central axis of the annular electrode. The electron gun is disposed on the central axis at distance along the axis from the annular anode, so that the x-ray source has a funnel-shape, and thus has a relatively large structural length.

As an alternative to this known structure, it is possible to inject the electron beam tangentially into the x-ray source, with the electron gun being disposed in the plane of the annular anode, or immediately next to the plane. The electron beam is annularly guided by deflection means, such as deflecting coils, so as to be deflected onto the annular anode for scanning thereof. The electron beam is incident on the anode at a focal spot, and causes the generation of an x-ray beam emanating from that focal spot on the annular anode. The x-ray beam is gated so as to be fan-shaped, and, by the deflection of the electron beam the focal spot, and thus the x-ray beam, is caused to rotates around the central axis of the measuring field so as to scan an examination subject in the measuring field from different angles. An annular x-ray detector acquires the x-rays attenuated by the examination subject, with the intensity of the incident radiation being converted into corresponding electrical signals, which are supplied to a computer which calculates an image of the examined slice of the examination subject therefrom.

The electron beam will typically have a current intensity on the order of magnitude of up to 1 A, given energies of 100 through 120 KeV. In order to obtain the focal spot necessary for computer tomography, the cross section of the electron beam can be circular or elliptical, with a diameter in the range of approximately 0.5 through 1 mm. In computer tomography, it is required that the x-ray beam rotate around the patient with a scan time of 30 through 100 ms, during which time a minimum angle of 180°, plus the beam fan angle, for example a total of 220°, must be described.

In order to guide the electron beam annularly, deflection means such as coils must be provided. As a consequence of space charge, however, the electron beam will nonetheless tend to widen, and such widening cannot be completely compensated by the deflection means functioning as a focusing device.

The space charge of the electrons can be compensated or neutralized by ions. For example, this can be accomplished by introducing gases into the vacuum vessel of the x-ray source, at pressures on the order of magnitude of $10^{-5}$ through $10^{-6}$ millibars. The gases are ionized by interaction with the electron beam. So-called residual gas ions which arise in this manner are generated in the time of few microseconds after the electron beam is activated, and thereafter cause a self-focusing of the electron beam.

If the electron beam were to be employed in the manner of a trace beam for the x-ray generation, such ionization would not build up, and the necessary self-focusing would not occur. The electron beam would diverge, and would impinge the walls of the housing after a few centimeters.

The focusing demands are only slightly less critical if the electron beam is guided in an annular channel having a diameter larger than 1 mm, i.e., for example, a few millimeters. With suitable, additional magnetic fields, an adaptation of the focusing must then be undertaken when the electrons are injected into their path of travel, and when they are deflected onto the annular electrode. In this case, however, it is difficult to generate a focal spot size which satisfies the demands of computer tomography, and which is constant over the entire annular anode.

SUMMARY OF THE INVENTION

It is an object of the present invention to provide a computer tomography apparatus having an annularly guided electron beam wherein a well-focused scanning of the annular anode is achieved.

The above object is achieved in accordance with the principles of the present invention in a computer tomography apparatus having an annular x-ray source wherein the electron beam is controlled by deflection means so that, before the beginning of a scanning event, the electron beam travels through the x-ray source concentrically relative to the annular anode until it is incident on a beam interceptor (i.e., a beam catcher, or beam collector) at a closed end of the x-ray source. Proceeding from this beam interceptor, the electron beam scans the annular electrode while being focused thereon. As a result of the transit of the electron beam through the x-ray source prior to beginning scanning of the annular anode, ions are formed over the entire length of the x-ray source, which act to focus and stabilize the electron beam in the manner discussed above. The generation of x-rays does not initially occur, and the build-up of the electron beam lasts a few microseconds. After 10 to 20 microseconds, the electron beam, by activation of an appropriately migrating magnetic field, is steadily deflected onto the annular anode beginning from that side facing the beam interceptor. X-rays are generated by the incidence of the electron beam on the annular anode. The x-ray beam generated in this manner, and the beam focus, continuously migrate proceeding from that end of the x-ray source facing the beam interceptor to the other end thereof.

DESCRIPTION OF THE DRAWINGS

The single FIGURE is a schematic view of a computer tomography apparatus having an annular x-ray source constructed in accordance with the principles of the present invention.

DESCRIPTION OF THE PREFERRED EMBODIMENTS

As shown in the drawing, a computer tomography apparatus constructed in accordance with the principles of the present invention has an annular x-ray source 2 which surrounds a measuring field 1. An annular anode 3 is disposed in the annular x-ray source 2. The annular anode 3 is to be scanned by an electron beam 5, generated by an electron gun 6, for the purpose of generating a rotating, fan-shaped x-ray beam 4. The electron gun 6 is followed by focusing coils 7. A vacuum is maintained in the x-ray source 2 by vacuum pumps 8.

For generating the x-ray beam 4, the electron beam 5 is directed onto the annular anode 3 using a magnetic deflecting coil 9. The x-rays after penetrating the examination subject, disposed in the measuring field 1, are acquired by an annular radiation detector 10, consisting of a row of detector elements. Each detector element generates an electrical signal corresponding to the intensity of x-ray incident thereon, with the output signals of the detector elements 10a, etc., being supplied to a computer 11. The computer 11 calculates an image of the examined slice of the examination subject in a known manner from the output signals of the detector elements and this image is portrayed on a monitor 12.

The measuring field 1 is present in an opening 13, into which the examination subject is introduced. As a result of deflection of the electron beam 5 onto the annular anode 3, the x-ray beam 4 rotates around the axis 4a, so that the examination subject is transilluminated from different directions.

A control unit 14 controls the deflecting coil 9 so that the electron beam 5, before the beginning of a scanning event, travels through the x-ray source 2 concentrically relative to the annular anode 3, until the electron beam 5 is incident on a radiation interceptor 15 consisting of, for example, lead, disposed at a closed end of the x-ray source 2. Before reaching the radiation interceptor 15, the electron beam 5 is defocused by a defocusing element 16.

From the beam interceptor 15, the electron beam is deflected onto the annular anode 3 by the deflecting coil 9, and scans the annular anode 3 from its end 17 to its end 18. Five focus positions are shown in the drawing, however in actuality there will be significantly more focused positions, for example, one-thousand such positions. The x-ray beam 4 thus rotates in a direction opposite to the direction of travel of the electron beam 5, and is situated in its final position as shown in the drawing. When the focal spot reaches the end 18, this constitutes the end of a scanning event.

Another build-up of the annularly guided electron beam 5 then follows, the beam again being initially incident on the beam catcher 15. A new scanning event begins with the deflection of the electron beam 5 starting at the end 17 of the annular anode 3.

The above-described scanning of the annular anode 3 results in a controlled, steady and stable focusing of the electron beam 5 over the entire length of the annular anode 3. A compensation of space charge fails to occur only over the final path length of the electron beam 5, after it is bent out of the annular orbit onto the annular anode 3. At this location, however, a slight beam spread (divergency) is acceptable, and is in fact exploited in order to achieve the desired focus size on the annular anode 3. This focus size is defined by the electrical and geometrical values of the x-ray source 2. The focus size is thus constant over the entire annular anode 3 from its end 17 to its end 18.

The radiation detector 10 is arranged with respect to the annular anode 3 so that the x-ray beam 4 can travel past it before the x-ray beam 4 enters into the measuring field 1. The x-ray beam 4 is thus incident on the radiation detector 10 only after it has emerged from the measuring field 1.

Although modifications and changes may be suggested by those skilled in the art, it is the intention of the inventor to embody within the patent warranted hereon all changes and modifications as reasonably and properly come within the scope of his contribution to the art.

I claim as my invention:

1. A computer tomography apparatus comprising;

an annular x-ray source surrounding a measuring field, said x-ray source having an annular anode and including means for generating an electron beam disposed at one end of said x-ray source and a beam interceptor disposed at an opposite end of said x-ray source;

deflection means for conducting said electron beam through said annular x-ray source, before beginning a scan event, concentrically relative to said annular anode so that said electron beam is incident on said beam interceptor; and means for scanning said annular anode with said electron beam in a direction proceeding from said beam interceptor toward said means for generating an electron beam by moving said electron beam over said annular anode around said annular x-ray source, after said electron beam was incident on said beam interceptor, with said electron beam being focused on said annular anode for generating an x-ray beam which rotates around said measuring field.

2. A computer tomography apparatus as claimed in claim 1 further comprising:

means for defocusing said electron bean disposed in said x-ray source preceding said beam interceptor.

3. A computer tomography apparatus as claimed in claim 1 wherein said x-ray source has electrical and geometrical values for causing a divergency of said electron beam for achieving a desired focus size of said electron beam on said annular anode.

4. A computer tomography apparatus as claimed in claim 1 wherein said annular anode is continuous and wherein said means for scanning moves said electron beam continuously over said annular anode around said annular x-ray source.

5. A method for operating a computer tomography apparatus having an annular x-ray source with an annular anode, said x-ray source containing an ionizable gas, said method comprising the steps of:

directing an electron beam through said x-ray source concentrically relative to said annular anode prior to beginning a scan event so as to ionize said ionizable gas in said x-ray tube;

intercepting said electron beam at an end of said x-ray source; and scanning said electron beam, after interception thereof, over said annular anode to generate a rotating x-ray beam in a measuring field while said x-ray beam is focused onto said anode by interaction with the ionized gas in said x-ray source.

* * * * *